US008071080B2

(12) United States Patent
Giroud

(10) Patent No.: US 8,071,080 B2
(45) Date of Patent: Dec. 6, 2011

(54) ORGANIC SALT CONDITIONER, ORGANIC SALT-CONTAINING COMPOSITION, AND USES THEREOF

(75) Inventor: Franck Giroud, Clichy (FR)

(73) Assignee: L'Oreal, Paris (FR)

( * ) Notice: Subject to any disclaimer, the term of this patent is extended or adjusted under 35 U.S.C. 154(b) by 1410 days.

(21) Appl. No.: 10/436,242

(22) Filed: May 13, 2003

(65) Prior Publication Data

US 2004/0005286 A1    Jan. 8, 2004

(30) Foreign Application Priority Data

May 14, 2002  (FR) ..................... 02 05913

(51) Int. Cl.
    *A61K 7/075*    (2006.01)
(52) U.S. Cl. ................. 424/70.27; 424/70.28
(58) Field of Classification Search ........... 424/70.27
    See application file for complete search history.

(56) References Cited

U.S. PATENT DOCUMENTS

| | | | |
|---|---|---|---|
| 3,989,711 A | 11/1976 | Bodor | |
| 5,364,625 A * | 11/1994 | Sebag et al. | 424/401 |
| 6,548,051 B2 * | 4/2003 | Garnier et al. | 424/70.1 |

FOREIGN PATENT DOCUMENTS

| | | | |
|---|---|---|---|
| EP | 1 182 196 | | 2/2002 |
| EP | 1 182 197 | | 2/2002 |
| EP | 1182196 | * | 2/2002 |
| EP | 1182196 A1 | * | 2/2002 |
| JP | 2002-003478 | * | 1/2002 |

OTHER PUBLICATIONS

Hawley's Condensed Chemical Dictionary. 12$^{th}$ edition (1993), p. 936.*
Nobuo Kimizuka et al.; "Spontaneous Self-Assembly of Glycolipid Bilayer Membranes in Sugar-philic Ionic Liquids and Formation of Ionogels"; Langmuir, vol. 17, 2001; pp. 6759-6761.
Michael Freemantle; "New Horizons for Ionic Liquids"; Chemical and Engineering News, 2001; pp. 21-25.
Database WPI; Week 200245; Derwent Publications Ltd., London, GB; AN 2002-419661 & JP 2002 003478 A; Jan. 9, 2002.
Derwent Publications Ltd., London, GB; AN 2002-419661, (2002). Spontaneous Self-Assembly of Glycolipid Bilayer Membranes in Sugar-philic Ionic Liquids and Formation of Ionogels, (2001).
M. Freemantle: New Horizons for Ionic Liquids, Chemical and Engineering News, 2001, pp. 21-25.

* cited by examiner

*Primary Examiner* — Jake M. Vu
(74) *Attorney, Agent, or Firm* — Oblon, Spivak, McClelland, Maier & Neustadt, L.L.P.

(57) ABSTRACT

The present invention relates to the use of, and a composition containing, at least one non-polymeric organic salt with a melting point of less than 60° C. These organic salts may be imidazolium, pyrazolium, pyridinium, pyrimidinium or tetraalkylphosphonium salts. The invention composition may be used for washing (cleaning) and/or conditioning keratin materials, and especially the hair.

22 Claims, No Drawings

ORGANIC SALT CONDITIONER, ORGANIC SALT-CONTAINING COMPOSITION, AND USES THEREOF

SUMMARY OF THE INVENTION

The present invention relates to a composition, preferably a cosmetic composition, comprising at least one particular organic salt, and to its use for, for example, washing and/or conditioning keratin materials. The invention also relates to the use of a particular organic salt, for example in cosmetics, as an agent for conditioning, and also to a cosmetic treatment process using the salt and the composition.

BACKGROUND OF THE INVENTION

It is especially sought in the cosmetics field to improve the conditioning of keratin materials, and in particular the hair. The term "conditioning" means properties of ease of disentangling, sheen and soft feel.

Fluid compounds with a low surface tension, such as silicones, are generally used for this purpose. They are well known in the art for improving in particular the disentangling of the hair.

Quaternary ammonium salts with a high melting point, such as cetrimonium bromide, in the form of an aqueous solution or an aqueous emulsion, may also be used for this purpose. With these two types of compounds, excellent conditioning of the hair may thus be obtained, but their use is accompanied by major drawbacks. Specifically, the hair becomes greasy, has a laden feel and a transfer of material onto the fingers is observed.

There are not currently, in this field, any other liquid lubricant compounds that afford excellent conditioning of the hair without the major drawbacks mentioned above.

DETAILED DESCRIPTION OF THE INVENTION

The inventor has found, surprisingly, that by using a particular family of compounds it is possible to obtain very good conditioning of the hair and to overcome the drawbacks of the compounds mentioned above, used in the cosmetic compositions of the prior art. This particular family of compounds is non-polymeric organic salts with a melting point of less than 60° C.

These organic salts form part of a general class of compounds that are well known as "Room Temperature Ionic Liquids" or RTIL. These RTILs generally have a melting point of less than 100° C. and remain liquid up to a temperature of about 300° C.

These RTILs are especially described in "Eyes on Ionic Liquids, Chemical and Engineering News", May 15, 2000, Vol. 78, 20, pages 37-50 and in "New Horizons for Ionic Liquids, Chemical and Engineering News", Jan. 1, 2001, Vol. 79, 1, pages 21-25.

The melting point is measured by differential calorimetric analysis (DSC) with a rate of temperature increase of 10° C./minute. The melting point is then the temperature corresponding to the top of the endothermic melting peak obtained during the measurement.

The organic salts of the invention also have excellent solvating power and excellent electrical conductivity. They are also non-volatile and non-flammable.

Another advantage of these organic salts lies in the fact that they are readily recycled and are among the solvents known as "green" solvents.

One subject of the invention is thus a (cosmetic) composition comprising at least one non-polymeric organic salt with a melting point of less than 60° C., where "(cosmetic)" refers to a preferable, but not necessary, characteristic of the composition.

Another subject of the present invention is a use of at least one non-polymeric organic salt with a melting point of less than 60° C., optionally present in a (cosmetic) composition, for washing (cleaning) and/or conditioning and/or otherwise treating (i.e., caring for) keratin materials, and in particular the hair.

A further subject of the invention is the use of a non-polymeric organic salt with a melting point of less than 60° C. as an agent for conditioning keratin materials, and in particular the hair.

A further subject of the present invention is a process for treating keratin materials using the non-polymeric organic salt with a melting point of less than 60° C. and/or the (cosmetic) composition according to the invention.

A further subject of the present invention is a process for modifying a (cosmetic) composition comprising adding thereto at least one non-polymeric organic salt with a melting point of less than 60° C., preferably in an amount sufficient to clean, condition, or otherwise treat keratin material.

Further subjects, characteristics, aspects and advantages of the invention will emerge upon reading the description and the various examples that follow.

The (cosmetic) composition according to the invention comprises, preferably in a cosmetically acceptable medium, at least one non-polymeric organic salt with a melting point of less than 60° C. This melting point is preferably less than 20° C., better still less than 0° C. and even more preferably less than −30° C., these limit ranges including all values and subranges therein as if specifically written out.

The expression "cosmetically acceptable medium" means a medium that is compatible with any keratin material such as the skin, the hair, the nails, the eyelashes, the eyebrows, the lips and any other area of the body and the face.

Preferably, the organic salts used in the composition according to the invention may be chosen from imidazolium, pyrazolium, pyridinium, pyrimidinium and tetraalkylphosphonium salts with a melting point of less than 60° C., preferably less than 20° C., better still less than 0° C. and even more preferably less than −30° C. and mixtures thereof.

Useful imidazolium salts include those of formula (I):

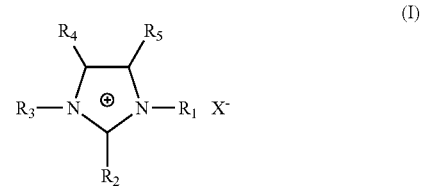

in which:
$R_1$ and $R_3$, which may be identical or different, each represent an alkyl group containing from 1 to 12 carbon atoms, preferably from 1 to 5 carbon atoms and better still from 1 to 4 carbon atoms,
$R_2$, $R_4$ and $R_5$, which may be identical or different, each represent a hydrogen atom or an alkyl group containing from 1 to 4 carbon atoms and preferably from 1 to 3 carbon atoms, and
$X^-$ represents an anion.

The alkyl groups may be linear or branched. Examples include methyl, ethyl, n-propyl, isopropyl, n-butyl, tert-butyl, pentyl, hexyl, octyl, nonyl, decyl and dodecyl groups.

Alkylmethylimidazolium salts and more specifically 1-butyl-3-methylimidazolium or 1-ethyl-3-methylimidazolium salts are preferably used herein.

Useful pyrazolium salts that may be used in the present invention include those of formula (II):

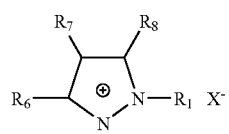

(II)

in which:

$R_1$ and $X^-$ have the same meaning as above (an alkyl group containing from 1 to 12 carbon atoms, preferably from 1 to 5 carbon atoms and better still from 1 to 4 carbon atoms, and an anion, respectively), and $R_6$, $R_7$ and $R_8$, which may be identical or different, each represent a hydrogen atom or an alkyl group containing from 1 to 5 carbon atoms and preferably from 1 to 4 carbon atoms.

Useful pyridinium salts that may be used in the invention include those of formula (III):

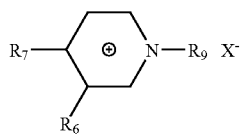

(III)

in which $R_6$, $R_7$ and $X^-$ are as defined above (a hydrogen atom or an alkyl group containing from 1 to 5 carbon atoms and preferably from 1 to 4 carbon atoms and an anion, respectively), and $R_9$ represents an alkyl group containing from 1 to 8 carbon atoms and preferably from 1 to 4 carbon atoms, and more particularly N-butylpyridinium salts.

Useful pyrimidinium salts that may be used in the present invention include those of formulae (IV) and (IV'):

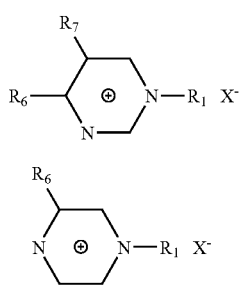

in which $R_1$, $R_6$, $R_7$ and $X^-$ are as defined above.

Other organic salts exist in the form of non-heterocyclic cations such as tetraalkylphosphonium salts with a melting point of less than 60° C.

Useful tetraalkylphosphonium salts that may be used in the present invention include those of formula (V):

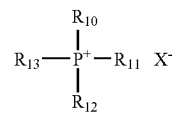

(V)

in which $R_{10}$, $R_{11}$, $R_{12}$ and $R_{13}$, which may be identical or different, represent an alkyl group containing from 1 to 18 carbon atoms and preferably from 1 to 14 carbon atoms, and $X^-$ represents an anion.

The anion present in the organic salt, for example that represented by $X^-$ in the above formulae, may be any anion known in the art, including a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_3CO_2^-$), an acetate ion ($CH_3CO_2^-$), a trifluoroacetate ion ($CF_3CO_2^-$) or a trifluoromethanesulphonate ion ($CF_3SO_3^-$).

Particularly preferred anions include the chloride, bromide, sulphate, acetate, tetrafluoroborate, hexafluorophosphate, triflate, nonaflate, bis(triflyl)amide and heptafluorobutanoate ions.

Particularly useful examples of organic salts that may be used in the context of the present invention include the following organic salts:
1-ethyl-3-methylimidazolium chloride,
1-ethyl-3-methylimidazolium bromide,
1-butyl-3-methylimidazolium chloride,
1-hexyl-3-methylimidazolium chloride,
1-methyl-3-octylimidazolium chloride,
1-decyl-3-methylimidazolium chloride,
1-decyl-3-methylimidazolium bromide,
1-dodecyl-3-methylimidazolium chloride,
1-methyl-3-tetradecylimidazolium chloride,
4-methyl-N-butylpyridinium chloride,
3-methyl-N-butylpyridinium chloride,
4-methyl-N-hexylpyridinium chloride,
1-ethyl-3-methylimidazolium tetrafluoroborate,
1-butyl-3-methylimidazolium tetrafluoroborate,
1-pentyl-3-methylimidazolium tetrafluoroborate,
1-hexyl-3-methylimidazolium tetrafluoroborate,
1-heptyl-3-methylimidazolium tetrafluoroborate,
1-octyl-3-methylimidazolium tetrafluoroborate,
1-nonyl-3-methylimidazolium tetrafluoroborate,
1-decyl-3-methylimidazolium tetrafluoroborate,
4-methyl-N-butylpyridinium tetrafluoroborate,
1-hexyl-3-ethylimidazolium tetrafluoroborate,
1-ethyl-3-methylimidazolium hexafluorophosphate,
1-butyl-3-methylimidazolium hexafluorophosphate,
1-pentyl-3-methylimidazolium hexafluorophosphate,
1-hexyl-3-methylimidazolium hexafluorophosphate,
1-heptyl-3-methylimidazolium hexafluorophosphate,
1-octyl-3-methylimidazolium hexafluorophosphate,
1-nonyl-3-methylimidazolium hexafluorophosphate,
1-decyl-3-methylimidazolium hexafluorophosphate,
1,3-dimethylimidazolium methylsulphate,
1-methyl-3-butylimidazolium methylsulphate,
1-ethyl-3-methylimidazolium nitrate,
1-ethyl-3-methylimidazolium nitrite, 1-ethyl-3-methylimidazolium acetate,
1-ethyl-3-methylimidazolium sulphate,
1-ethyl-3-methylimidazolium triflates,
1-ethyl-3-methylimidazolium nonaflates,
1-ethyl-3-methylimidazolium bis(triflyl)amide,
1-butylpyridinium bromide,
1-butylpyrimidinium trifluoromethanesulphonate,
1-hexylpyrimidinium trifluoromethanesulphonate,
1-ethyl-3-methylimidazolium trifluoroacetate,
trihexyltetradecylphosphonium chloride,
tributyltetradecylphosphonium chloride,
1-ethyl-2-methylpyrazolium tetrafluoroborate, and
1-methyl-3-butylpyrimidinium tetrafluoroborate.

It is possible to modify the chemistry of organic salts, including those described above, so as to vary their solubility. To preserve the meltability of these salts at low temperature, it is preferable to more specifically modify the alkyl chains partially constituting the organic salts. In this context, examples include the etherification of the alkyl chain of the salts of the 1-alkyl-3-methylimidazolium family, which affords the compounds of the following formulae:

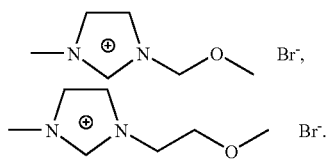

Such a chemical modification confers or reinforces the organic salt's water-soluble nature, without losing the low-temperature meltability of the salt. Such a chemical modification may also allow the organic salts to be gelled by combination with amphiphilic sugars and make it possible to obtain what is known as ionogels. Such properties are described in the article "*Spontaneous Self assembly of glycolipid bilayer Membranes in Sugar-philic Ionic Liquids and formation of Ionogels*" published by N. Kimizuka and T Nakashima (Langmuir 17, 6759-6761, (2001)).

The organic salt or the mixture of organic salts described above is preferably present in the (cosmetic) compositions of the invention in a concentration of between 0.00001% and 99.9999% by weight, more preferably between 0.01% and 50% by weight and better still between 0.1% and 30% by weight, relative to the total weight of the composition, all values and subranges between these ranges being specifically included as if written out.

The organic salt or the mixture of organic salts may be in any form, for example, solution or in the form of an emulsion. The organic salt or the mixture of organic salts may also be microencapsulated before being incorporated into the cosmetic composition.

The organic salt as described above is especially preferably used, for example in cosmetics, as a conditioner.

The cosmetically acceptable medium of the cosmetic composition of the invention may contain a cosmetically acceptable compound or a mixture of cosmetically acceptable compounds to convey the organic salts. This vehicle may in a preferred embodiment comprise of one of the following compounds or a mixture of two or more of the following compounds: water; $C_1$-$C_4$ aliphatic alcohols and more particularly ethanol; aromatic alcohols such as benzyl alcohol; saturated or unsaturated $C_{10}$-$C_{30}$ fatty alcohols; modified or unmodified polyols such as glycerol, propylene glycol, dipropylene glycol, butylene glycol, butyl diglycol or polyethylene glycols; volatile or non-volatile silicones such as cyclopentasiloxane, polydimethylsiloxanes optionally modified with phenyl and/or siloxy and/or silanol and/or amine and/or imine and/or fluoroalkyl and/or carboxyl and/or betaine and/or quaternary ammonium functions; mineral, organic or plant oils; oxyethylenated or non-oxyethylenated waxes, paraffins; alkanes and more particularly $C_5$-$C_{10}$ alkanes; $C_{10}$-$C_{30}$ fatty acids; $C_{10}$-$C_{30}$ fatty amides, $C_{10}$-$C_{30}$ fatty esters and more particularly fatty alkyl benzoates or salicylates.

The cosmetically acceptable medium may also comprise at least one other compound such as acetone, methyl ethyl ketone, methyl acetate, butyl acetate, ethyl acetate, dimethoxyethane or diethoxyethane.

The composition according to the invention may also comprise a propellant. Propellants that may especially be mentioned include the compressed or liquefied gases generally used for preparing aerosol compositions. Examples of propellants that may especially be mentioned include air, carbon dioxide, compressed nitrogen or a soluble gas such as dimethyl ether, halogenated hydrocarbons, for example fluorinated hydrocarbons, or non-halogenated hydrocarbons, and mixtures thereof.

The compositions of the invention may also contain one or more cosmetic additives, including those currently commonly used in the art, such as, for example, reducing agents, oxidizing agents, fatty substances, silicones, thickeners, softeners, antifoams, moisturizers, emollients, basifying agents, plasticizers, sunscreens, direct dyes or oxidation dyes, pigments, mineral fillers, clays, colloidal minerals, nacres, fragrances, peptizers, preserving agents, anionic, amphoteric, zwitterionic or nonionic surfactants, fixing or non-fixing polymers, conditioning polymers, proteins and vitamins. A person skilled in the art is able to select the optional cosmetic additives and the amount thereof such that they preferably do not harm, at least to a great extent, the properties of the compositions of the present invention. As a guide, these adjuvants are generally present in the composition according to the invention in an amount ranging from 0 to 20% by weight relative to the total weight of the composition.

The cosmetic compositions of the invention may be in any of various presentation forms, such as a lotion, a spray, a mousse, a conditioner or a shampoo.

When the composition is used for washing and/or conditioning keratin materials, especially the hair, it may be used in rinse-out or leave-in mode.

The (cosmetic) treatment process according to the invention comprises applying to one or more keratin materials a (cosmetic) composition according to the invention for example at a temperature of between 10 and 80° C., and optionally in rinsing the materials after an action time of, for example, between 15 seconds and 30 minutes. As an alternative, one can simply apply the organic salt.

The examples that follow are given as illustrations of the present invention, and are not limiting thereof

EXAMPLE 1 AND COMPARATIVE EXAMPLE 1

Rinse-Out Compositions

Example 1 concerns a shampoo according to the invention, while Comparative Example 1 concerns a control shampoo.

The shampoos are prepared from the ingredients below, in the following proportions indicated as % by weight.

|  | Ex. 1 | Comp. Ex. 1 |
|---|---|---|
| Sodium laureth sulphate[1] | 30 AM | 30 AM |
| Cocobetaine[2] | 4 AM | 4 AM |
| Cocamide MIPA[3] | 2 AM | 2 AM |
| PDMS (PM 250 000)[4] | — | 1.5 AM |
| 1-Methyl-3-butlimidazolium tetrafluoroborate[5] | 1.5 AM | — |
| Sodium cetearyl sulphate[6] | 0.8 AM | 0.8 AM |
| Polyquaternium-10[7] | 0.4 AM | 0.4 AM |
| Carbomer[8] | 0.2 AM | 0.2 AM |
| Propylene glycol | 0.1 AM | 0.1 AM |
| Preserving agent | qs | qs |
| Fragrance | qs | qs |
| Water qs | 100 | 100 |

A.M.: active material
[1]Texapon N 702 sold by the company Cognis,
[2]Dehyton AB 30 OR sold by the company Cognis,
[3]Empilan CIS sold by the company Hunstman,
[4]Mirasil DM 500 000 sold by the company Rhodia,
[5]sold by the company Solvent Innovation GmbH under the reference 99,020-1,
[6]Lanette E sold by the company Cognis,
[7]Ucare Polymer JR 400 sold by the company Amerchol,
[8]Carbopol 980 sold by the company Noveon.

These two shampoo formulations were then subjected to evaluation of the cosmetic characteristics imparted to the hair.

5 g of shampoo were applied to a head of hair consisting of natural chestnut-brown Caucasian hair 20 cm long. After leaving the shampoo to act for 2 minutes, the head of hair was rinsed with water and then styled using a hairdryer.

This test was performed on 20 models: 10 models with the shampoo of Example 1 and the other 10 with the shampoo of Comparative Example 1.

The cosmetic characteristics of the heads of hair were then evaluated by a panel of 10 experts.

This panel indicated that all the heads of hair treated with the shampoo of Example 1, i.e. the shampoo of the invention, were softer, smoother and felt less greasy and less laden than the heads of hair treated with the shampoo of Comparative Example 1.

EXAMPLE 2 AND COMPARATIVE EXAMPLE 2

Leave-In Compositions

Example 2 concerns a sheen cream according to the invention, whereas Comparative Example 2 concerns a control sheen cream.

The sheen creams are prepared from the ingredients below, in the following proportions indicated as % by weight.

|  | Ex. 2 | Comp. Ex. 2 |
|---|---|---|
| Cyclopentasiloxane[1] | — | 10 AM |
| 1-Methyl-3-butylimidazolium tetrafluoroborate[2] | 10 AM | — |
| Cyclopentasiloxane dimethicone copolyol[3] | 0.5 AM | 0.6 AM |
| Propylene glycol | 2.5 AM | 2.5 AM |
| Preserving agent | qs | qs |
| Fragrance | qs | qs |
| Water qs | 100 | 100 |

A.M.: active material
[1]Mirasil CM 5 sold by the company Rhodia,
[2]sold by the company Solvent Innovation GmbH under the reference 99,020-1,
[3]Dow Corning 5225C sold by the company Dow Corning.

These two sheen cream formulations were then subjected to evaluation of the cosmetic characteristics imparted to the hair.

5 g of sheen cream were applied to a head of hair consisting of natural chestnut-coloured Caucasian hair 20 cm long.

This test was performed on 20 models: 10 models with the sheen cream of Example 2 and the other 10 with the sheen cream of Comparative Example 2.

The cosmetic characteristics of the heads of hair were then evaluated by a panel of 10 experts, after an action time of 10 minutes.

This panel indicated that all the heads of hair treated with the sheen cream of Example 2, i.e. the sheen cream of the invention, felt less greasy and less laden than the heads of hair treated with the sheen cream of Comparative Example 2. In addition, the heads of hair treated with the sheen cream of Example 2 were shinier.

The above written description of the invention provides a manner and process of making and using it such that any person skilled in this art is enabled to make and use the same, this enablement being provided in particular for the subject matter of the appended claims and including a (cosmetic) composition comprising, preferably in a cosmetically acceptable medium, at least one non-polymeric organic salt with a melting point of less than 60° C., as well as the use of such a composition or salt for, e.g., washing and/or conditioning keratin materials, in particular the hair, as well as a (cosmetic) process for treating keratin materials, in particular the hair, which comprises applying to keratin materials the invention composition or salt, for example at a temperature of between 10 and 80° C., and optionally including rinsing out the composition after an action time of, e.g., between 15 seconds and 30 minutes. Other preferred embodiments enabled herein include a process for modifying a (cosmetic) composition comprising adding thereto at least one non-polymeric organic salt with a melting point of less than 60° C., preferably in an amount sufficient to clean, condition, or otherwise treat keratin material, a method for cleaning, conditioning or otherwise treating keratin material comprising applying thereto at least one non-polymeric organic salt with a melting point of less than 60° C., a composition for cleaning, conditioning or otherwise treating keratin material comprising at least one non-polymeric organic salt with a melting point of less than 60° C., and a skin, hair, nail, eyelash, eyebrow or lip care composition comprising at least one non-polymeric organic salt with a melting point of less than 60° C.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

This application claims priority to French patent application 0205913, filed May 14, 2002, this French application being incorporated herein by reference.

The invention claimed is:
1. A method for cleaning, conditioning or otherwise treating keratin material comprising applying thereto at least one non-polymeric organic salt with a melting point of less than 60° C. selected from the group consisting of imidazolium, pyrazolium, pyridinium, pyrimidinium and tetraalkylphosphonium salts, and mixtures thereof, wherein the imidazolium salt corresponds to the following formula:

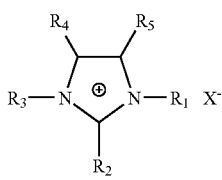

in which $R_1$ and $R_3$, which may be identical or different, each represent an alkyl group containing from 1 to 5 carbon atoms, $R_2$, $R_4$ and $R_5$, which may be identical or different, each represent a hydrogen atom or an alkyl group containing from 1 to 4 carbon atoms, and $X^-$ represents an anion.

2. The method according to claim 1, wherein the non-polymeric organic salt has a melting point of less than 20° C.

3. The method according to claim 1, wherein X is selected from the group consisting of a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_2CO_2^-$), an acetate ion ($CH_3CO_2^-$), a trifluoroacetate ion ($CF_3CO_2^-$) and a trifluoromethanesulphonate ion ($CF_3SO_3^-$).

4. The method according to claim 1, wherein said salt is selected from the group consisting of:
1-ethyl-3-methylimidazolium chloride,
1-ethyl-3-methylimidazolium bromide,
1-butyl-3-methylimidazolium chloride,
1-hexyl-3-methylimidazolium chloride,
1-methyl-3-octylimidazolium chloride,
1-decyl-3-methylimidazolium chloride,
1-decyl-3-methylimidazolium bromide,
1-dodecyl-3-methylimidazolium chloride,
1-methyl-3-tetradecylimidazolium chloride,
4-methyl-N-butylpyridinium chloride,
3-methyl-N-butylpyridinium chloride,
4-methyl-N-hexylpyridinium chloride,
1-ethyl-3-methylimidazolium tetrafluoroborate,
1-butyl-3-methylimidazolium tetrafluoroborate,
1-pentyl-3-methylimidazolium tetrafluoroborate,
1-hexyl-3-methylimidazolium tetrafluoroborate,
1-heptyl-3-methylimidazolium tetrafluoroborate,
1-octyl-3-methylimidazolium tetrafluoroborate,
1-nonyl-3-methylimidazolium tetrafluoroborate,
1-decyl-3-methylimidazolium tetrafluoroborate,
4-methyl-N-butylpyridinium tetrafluoroborate,
1-hexyl-3-ethylimidazolium tetrafluoroborate,
1-ethyl-3-methylimidazolium hexafluorophosphate,
1-butyl-3-methylimidazolium hexafluorophosphate,
1-pentyl-3-methylimidazolium hexafluorophosphate,
1-hexyl-3-methylimidazolium hexafluorophosphate,
1-heptyl-3-methylimidazolium hexafluorophosphate,
1-octyl-3-methylimidazolium hexafluorophosphate,
1-nonyl-3-methylimidazolium hexafluorophosphate,
1-decyl-3-methylimidazolium hexafluorophosphate,
1,3-dimethylimidazolium methylsulphate,
1-methyl-3-butylimidazolium methylsulphate,
1-ethyl-3-methylimidazolium nitrate,
1-ethyl-3-methylimidazolium nitrite,
1-ethyl-3-methylimidazolium acetate,
1-ethyl-3-methylimidazolium sulphate,
1-ethyl-3-methylimidazolium triflates,
1-ethyl-3-methylimidazolium nonaflates,
1-ethyl-3-methylimidazolium bis(triflyl)amide,
1-butylpyridinium bromide,
1-butylpyrimidinium trifluoromethanesulphonate,
1-hexylpyrimidinium trifluoromethanesulphonate,
1-ethyl-3-methylimidazolium trifluoroacetate,
trihexyltetradecylphosphonium chloride,
tributyltetradecylphosphonium chloride,
1-ethyl-2-methylpyrazolium tetrafluoroborate,
1-methyl-3-butylpyrimidinium tetrafluoroborate, and
1-ethyl-3-methylimidazolium trifluoroacetate.

5. The method according to claim 1, wherein the organic salt is present in a composition in an amount of between 0.00001% and 99.9999% by weight, relative to the total weight of the composition.

6. The method according to claim 5, wherein the composition further comprises a cosmetically acceptable medium.

7. The method according to claim 6, wherein the cosmetically acceptable medium comprises at least one of water; $C_1$-$C_4$ aliphatic alcohols; aromatic alcohols; fatty alcohols; modified or unmodified polyols; volatile or non-volatile silicones; mineral, organic or plant oils; oxyethylenated or non-oxyethylenated waxes, paraffins; $C_5$-$C_{10}$ alkanes; fatty acids; fatty amides, and fatty esters.

8. The method according to claim 6, said composition further comprising at least one organic compound selected from the group consisting of acetone, methyl ethyl ketone, methyl acetate, butyl acetate, ethyl acetate, dimethoxyethane and diethoxyethane.

9. The method according to claim 6, said composition further comprising at least one cosmetic additive selected form the group consisting of reducing agents, oxidizing agents, fatty substances, silicones, thickeners, softeners, antifoams, moisturizers, emollients, basifying agents, plasticizers, sunscreens, direct dyes or oxidation dyes, pigments, mineral fillers, clays, colloidal minerals, nacres, fragrances, peptizers, preserving agents, anionic, amphoteric, zwitterionic or nonionic surfactants, fixing or non-fixing polymers, conditioning polymers, proteins and vitamins.

10. The method of claim 1, further comprising applying said salt to said keratin material at a temperature of between 10 and 80° C., and optionally rinsing out the salt after an application time of between 15 seconds and 30 minutes.

11. The method of claim 1, wherein said keratin material is hair.

12. The method of claim 1, comprising conditioning hair.

13. The method of claim 1, comprising cleaning hair.

14. The method according to claim 1, wherein the organic salt is selected from the group consisting of pyrazolium, pyridinium, pyrimidinium and tetraalkylphosphonium salts, and mixtures thereof.

15. The method according to claim 1, wherein said salt is a pyrazolium salt corresponding to the following formula:

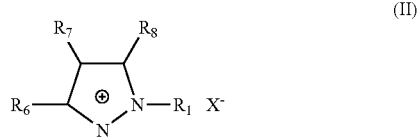

in which $R_1$ represents an alkyl group containing from 1 to 18 carbon atoms, $R_6$, $R_7$ and $R_8$, which may be identical or different, each represent a hydrogen atom or an alkyl group containing from 1 to 5 carbon atoms, and $X^-$ represents an anion.

16. The method according to claim 1, wherein said salt is a pyridinium salt corresponding to the following formula:

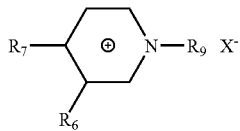

(III)

in which $R_9$ represents an alkyl group containing from 1 to 8 carbon atoms, $R_6$ and $R_7$, which may be identical or different, each represent a hydrogen atom or an alkyl group containing from 1 to 5 carbon atoms, and $X^-$ represents an anion.

17. The method according to claim 1, wherein said salt is a pyrimidinium salt corresponding to one of the following formulae:

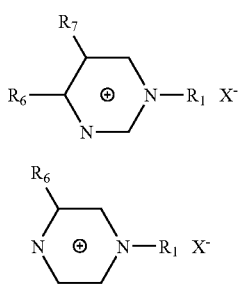

(IV)

(IV')

in which $R_1$ represents an alkyl group containing from 1 to 18 carbon atoms, $R_6$ and $R_7$, which may be identical or different, each represent a hydrogen atom or an alkyl group containing from 1 to 5 carbon atoms, and $X^-$ represents an anion.

18. The method according to claim 1, wherein said salt is a tetraalkylphosphonium salt corresponding to the following formula:

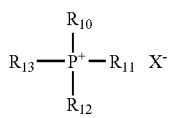

(V)

in which $R_{10}$, $R_{11}$, $R_{12}$ and $R_{13}$, which may be identical or different, represent an alkyl group containing from 1 to 18 carbon atoms, and $X^-$ represents an anion.

19. The method according to claim 15, wherein X is selected from the group consisting of a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_3CO_2^-$), an acetate ion ($CH_3CO_2^-$), a trifluoroacetate ion ($CF_3CO_2^-$) and a trifluoromethanesulphonate ion ($CF_3SO_3^-$).

20. The method according to claim 16, wherein X is selected from the group consisting of a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_3CO_2^-$), an acetate ion ($CH_3CO_2^-$), a trifluoroacetate ion ($CF_3CO_2^-$) and a trifluoromethanesulphonate ion ($CF_3SO_3^-$).

21. The method according to claim 17, wherein X is selected from the group consisting of a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_3CO_2^-$), an acetate ion ($CH_3CO_2^-$), a trifluoroacetate ion ($CF_3CO_2^-$) and a trifluoromethanesulphonate ion ($CF_3SO_3^-$).

22. The method according to claim 18, wherein X is selected from the group consisting of a chloride ion ($Cl^-$), a bromide ion ($Br^-$), a tetrachloroaluminate ion ($AlCl_4^-$), a tetrachloronickel ion ($NiCl_4^-$), a perchlorate ion ($ClO_4^-$), a nitrate ion ($NO_3^-$), a nitrite ion ($NO_2^-$), a sulphate ion ($SO_4^{2-}$), a methyl sulphate ion ($CH_3SO_4^-$), a tetrafluoroborate ion ($BF_4^-$), a hexafluorophosphate ion ($PF_6^-$), a hexafluoroantimonate ion ($SbF_6^-$), a triflate [TfO] ion ($CF_3SO_2^-$), a nonaflate [NfO] ion ($CF_3(CF_2)_3SO_2^-$), a bis(triflyl)amide [$Tf_2N$] ion (($CF_3SO_2)_2N^-$), a trifluoroacetate [TA] ion ($CF_3CO_2^-$), a heptafluorobutanoate [HB] ion ($CF_3(CF_2)_3CO_2^-$), an acetate ion ($CH_3CO_2^-$), a trifluoroacetate ion ($CF_3CO_2^-$) and a trifluoromethanesulphonate ion ($CF_3SO_3^-$).

* * * * *